United States Patent
Watson et al.

(10) Patent No.: US 6,686,507 B2
(45) Date of Patent: Feb. 3, 2004

(54) PURIFICATION OF 2-METHOXY-5-TRIFLUOROMETHOXYBENZALDEHYDE

(75) Inventors: Timothy J. N. Watson, Waterford, CT (US); Patrice Arpin, Sorel-Tracy (CA); Michael G. Vetelino, North Stonington, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/314,598

(22) Filed: Dec. 9, 2002

(65) Prior Publication Data

US 2003/0176741 A1 Sep. 18, 2003

Related U.S. Application Data

(60) Provisional application No. 60/361,931, filed on Mar. 6, 2002.

(51) Int. Cl.$^7$ ................................................ C07C 45/90
(52) U.S. Cl. ...................................................... 568/438
(58) Field of Search ........................................... 568/438

(56) References Cited

U.S. PATENT DOCUMENTS

| | | | |
|---|---|---|---|
| 4,192,949 A | 3/1980 | Merger et al. | 560/67 |
| 5,294,744 A | 3/1994 | Godek et al. | 568/442 |
| 5,773,450 A | 6/1998 | Lowe et al. | 514/329 |
| 5,807,867 A | 9/1998 | Ito et al. | 514/305 |

OTHER PUBLICATIONS

W. E. Smith, *Journal of Organic Chemistry*, vol. 37, No. 24, p. 3972 (1972).

Chemical Abstracts, 99(15), 1983, No. 122032.

*Primary Examiner*—James O. Wilson
*Assistant Examiner*—Sikarl A. Witherspoon
(74) *Attorney, Agent, or Firm*—Peter C. Richardson; Paul H. Ginsburg; Jolene W. Appleman

(57) ABSTRACT

A process for the purification of 2-methoxy-5-trifluoromethoxy benzaldehyde oil in which the oil is converted to amine by reaction of a nitroaniline with the oil; the imine is isolated as a solid; and the solid imine is converted back to the 2-methoxy-5-trifluoromethoxy benzaldehyde oil. The nitroaniline is selected from the group consisting of 3-nitroaniline, 3-methyl-2-nitroaniline, 4-methyl-2-nitroaniline, 2 methyl-3-nitroaniline and 4-methyl-3-nitroaniline.

6 Claims, No Drawings

PURIFICATION OF 2-METHOXY-5-TRIFLUOROMETHOXYBENZALDEHYDE

BACKGROUND OF THE INVENTION

This invention relates to a new and useful process for the purification of 2-methoxy-5-trifluoro-methoxy benzaldehyde by conversion to a series of nitroanilines. In particular, it is concerned with a novel two step process for purifying the oil, 2-methoxy-5-trifluoro-methoxybenzaldehyde, wherein the oil is first converted to a nitroaniline. The nitroaniline is isolated as a solid imine and then simply converted back to the oil, 2-methoxy-5-trifluoro-methoxybenzaldehyde. The result is a drastic reduction in the impurities seen in the commercial source which is the usual starting ingredient for the preparation of substance P receptor antagonists.

In accordance with the prior art U.S. Pat. No. 5,294,744 issued Mar. 15, 1994, there has already been described in a two-step reaction a process for preparing 5-substituted-2-methoxybenzaldehyde compounds wherein the substituent group is either isopropyl or trifluoromethoxy. The process involves (1) reacting a corresponding 4-substituted phenol compound with dimethyl carbonate in the presence of a tertiary-amine base to form the corresponding 4-substituted anisole compound. The second step (2) subjects the latter intermediate product obtained in the first step to aromatic C-formylation on the ring with hexamethylenetetramine in the presence of trifluoroacetic acid, followed by hydrolysis, to ultimately yield the desired aldehyde compound. The two aromatic aldehyde compounds so obtained, viz., 2-methoxy-5-trifluoromethoxybenzaldehyde and 2-methoxy-5-isopropylbenzaldehyde, are known to be useful as intermediates that specifically lead to (2S, 3S)-cis-3-(2-methoxy-5-trifluoromethoxylbenzyl)amino-2-phenylpiperidine and (2S, 3S)-cis-2-(diphenylmethyl)-N-[(2-methoxy-5-isopropylphenyl)-methyl]-1-azabicyclo[2.2.2]octane-3-amine, respectively. The latter final products, in turn, are both known to be useful in the field of medicinal chemistry as substance P receptor antagonists.

In accordance with the prior art, there has already been described certain compounds which are known to be of value as substance P receptor antagonists. Included among these are such nitrogen-containing heterocyclic ring compounds as (2S, 3S)-cis-3-(2-methoxy-5-trifluoromethoxylbenzyl)amino-2-phenylpiperidine, which is described and claimed by J. A. Lowe, III, et al., in U.S. Pat. No. 5,773,450, issued Jun. 30, 1998, and (2S, 3S)-cis-2-(diphenylmethyl)-N-[(2-methoxy-5-isopropylphenyl)-methyl]-1-azabicyclo[2.2.2]octane-3-amine, which is described and claimed by F. Ito, et al., in U.S. Pat. No. 5,807,867, issued Sep. 15, 1998. Both compounds are useful as non-steroidal anti-inflammatory (N.S.A.I.) agents, being of specific value in the treatment of arthritis, asthma and inflammatory bowel disease.

In the past, these particular compounds have been prepared by various synthetic means but essentially by a method which involves the reductive amination of the appropriate aldehyde compound, i.e., by reacting either the oily compound 2-methoxy-5-isopropylbenzaldehyde or 2-methoxy-5-trifluoromethoxybenzaldehyde, as the case may be, with the corresponding heterocyclic 3-amino compound in the presence of a source of hydrogen or else it can be made by first condensing the aforesaid 3-amino compound with the aldehyde and then reducing the resulting imine intermediate to ultimately give the key benzylamine side chain. The starting aromatic aldehyde component in this particular reaction scheme had always been prepared in two steps starting from the corresponding known and readily available 4-substituted phenol compound. This, in turn, initially involved (1) first methylating the phenol compound with methyl iodide in an acetone solvent medium in the presence of solid potassium carbonate, followed by (2) direct formylation of the resulting 4-substituted methylated phenol (i.e., 4-substituted anisole compound) with α-dichloromethyl methyl ether in a methylene chloride solvent system in the presence of titanium tetrachloride as catalyst. However, this particular two-step method for the production of the aldehyde suffers from the drawback of being conducted in a non-homogenous reaction system in the first step, with all its attendant disadvantages, and in employing the somewhat hazardous titanium tetrachloride reagent as catalyst in the second step. In the latter connection, it should be noted that certain stringent safety requirements are normally called for when handling the latter agent, particularly when unit operations are conducted on a large scale. Additionally, the use of various hazardous waste disposal techniques are also required for the removal of the titanium tetrachloride byproducts that are usually formed in the aforesaid aromatic formylation reaction.

In the past, F. Merger, et al. in the U.S. Pat. No. 4,129,949 indicate that they have prepared various methyl phenyl ethers, including both 4-methylanisole and 4-methoxyanisole, from the corresponding phenol compounds, using dimethyl carbonate in the presence of a tertiaryamine base as catalyst without the presence of a solvent. Although the Merger, et al. patent also includes p-isopropylphenol in a long list of many other possible phenolic starting materials for the aforementioned reaction, there is no indication that 4-isopropylanisole was ever actually prepared in this particular manner. On the other hand, W. E. Smith in the *Journal of Organic Chemistry*, Vol. 37, No. 24, p. 3972 (1972) reports on its direct C-formylation of several aromatic compounds, including 2,6-dimethylanisole, via a method which involves the use of hexamethylenetetramine in trifluoroacetic acid in a modified Duff reaction, but there is no indication in the aforesaid paper by Smith that such a reaction could ever be successfully carried out using other non-acidic derivatives of anisole as substrate. In particular, there is no indication that the reaction of Smith could be applied to parasubstituted derivatives of anisole.

SUMMARY OF THE INVENTION

A process for the purification of 2-methoxy-5-trifluoromethoxy benzaldehyde oil comprising converting the oil to an to amine by reacting of a nitroaniline with the oil; isolating the imine as a solid; and converting back the solid imine to the 2-methoxy-5-trifluoromethoxy benzaldehyde oil. The nitro-aniline is selected from the group consisting of 3-nitroaniline, 3-methyl-2-nitroaniline, 4-methyl-2-nitroaniline, 2-methyl-3-nitroaniline and 4-methyl-3-nitroaniline. The iminess are selected from the group consisting of (2-Methoxy-5-trifluoromethoxybenzylidene)-(3-nitrophenyl)amine;

(2-Methoxy-5-trifluoromethoxybenzylidene)-(4-mehtyl-2-nitrophenyl)amine;

(2-Methoxy-5-trifluoromethoxybenzylidene)-(3-mehtyl-2-nitrophenyl)amine;

(2-Methoxy-5-trifluoromethoxybenzylidene)-(2-methyl-3-nitrophenyl)amine;

(2-Methoxy-5-trifluoromethoxybenzylidene)-(4-mehtyl-3-nitrophenyl)amine;

(2-Methoxy-5-trifluoromethoxybenzylidene)-(4-nitrophenyl)amine;

(2-Methoxy-5-trifluoromethoxybenzylidene)-(3,5-dinitrophenyl)amine;

(2-Methoxy-5-trifluoromethoxybenzylidene)-(1,6-dinitrophenyl)amine;

(2-Methoxy-5-trifluoromethoxybenzylidene)-(2,4-dinitrophenyl)amine;

(2-Methoxy-5-trifluoromethoxybenzylidene)-(5-methyl-2-nitrophenyl)amine; and (2-Methoxy-5-trifluoromethoxybenzylidene)-(6-methyl-2-nitrophenyl)amine.

The temperature range in which to precipitate the imine is about 30 to about 40° C. The solvent used to recrystallize the imine is selected from the group consisting of ethanol, methanol and ethanol/hexane. The solvent used to recrystallze the 2-methoxy-5-trifluoromethoxy benzaldehyde is a mixture of hexane and hydrochloric acid.

DETAILED DESCRIPTION OF THE INVENTION

In accordance with the process of this invention, a purified solid from the oil, 2-methoxy-5-trifluoromethoxybenzaldehyde, was attempted by a protection reaction with its aldehyde functional group. Two ways were first investigated: either making the acetal or the imine. The acetal reactions were not successful. However, the second attempt using a nitroaniline compound gave a solid imine which was easily deprotected and gave a good yield. More importantly, the processes had highly-decreased the level of impurity of 2-methoxy-5-trifluoromethoxybenzaldehyde, now again in the oil form.

Scheme 1

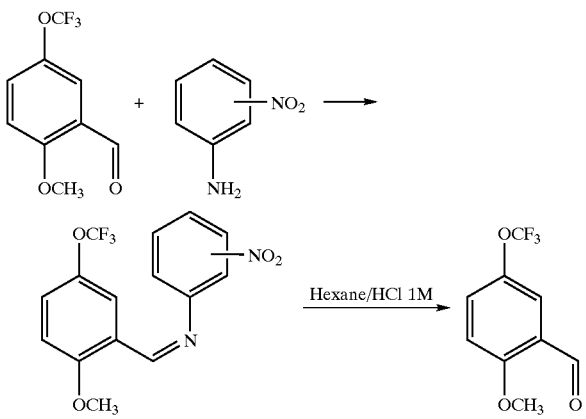

SCHEME 2 substrate descriptions:

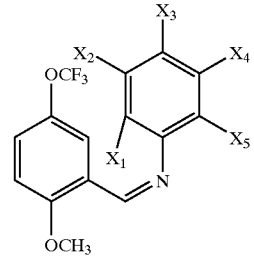

| | $X_1$ | $X_2$ | $X_3$ | $X_4$ | $X_5$ |
|---|---|---|---|---|---|
| 1 | — | — | — | $NO_2$ | — |
| 2 | — | — | $CH_3$ | — | $NO_2$ |
| 3 | — | — | — | $CH_3$ | $NO_2$ |
| 4 | — | — | — | $NO_2$ | $CH_3$ |
| 5 | — | — | $CH_3$ | $NO_2$ | — |
| 6 | — | — | $NO_2$ | — | — |
| 7 | — | $NO_2$ | — | $NO_2$ | — |
| 8 | $NO_2$ | — | — | — | $NO_2$ |
| 9 | — | — | $NO_2$ | — | $NO_2$ |
| 10 | — | $CH_3$ | — | — | $NO_2$ |
| 11 | $CH_3$ | — | — | — | $NO_2$ |

The idea behind the purification of the aldehyde was to make a solid from the oil and to filtered out the impurities. At first, the focus was on the possibility of making the acetal but that was without success. Next investigative reactions of imine formation were tried with some amines using nitroaniline analogues. This gave a solid very quickly and easily.

The imine formation implies equilibrium and most nitro compounds do not have good solubility in such solvent. But the high stability of the conjugated structure proposed by the imine drove the equilibrium to the formation of the imine. The difference of solubility between the original nitroaniline analogues and the imine helped to complete the reaction with a very good yield.

Having discerned that the main problem was to search for a good mixture of solvent that ensures a precipitation of the imine, it was possible to manage the solubility by controlling the temperature and the solvent composition. It was also possible to obtain a list of conditions to enhance imine formation. Adjusting the temperature gave better control of the reaction.

The best conditions were achieved with the 3-nitroaniline analogue. The solution was heated to 55° C. where it became homogeneous and then, the solution was slowly cooled to 31–34° C. where precipitation started. For 1 hour, the solution was stirred between 34–37° C. to get a better crystallization. The solution was slowly cooled down to 0° C., filtered and washed with cold hexane.

Because the solid imine is stabilized by its conjugated structure, it is possible to recrystallized it at high temperature without decomposing it. Analysis on the 3-nitroaniline imine complex showed that the recrystallization processes give only one isomer. By keeping the solid in solution, NMR shows its transformation to other isomers with time. This suggests that the imine is in equilibrium between its geometric isomers.

The deprotection reaction implies that there is a biphasic system in which the imine is stirred for a certain time. The acid aqueous layer stabilizes the amine and the benzaldehyde showed a great solubility in hexane. Depending on the nitroaniline analogue, it can take between 1 hour and 15 hours to form the imine.

It appears that the formation of the imine via the nitroaniline works best because of its easy reaction conditions and its defined recrystallization conditions. However, further investigation into the other amine analogues resulted in better conditions for most of the other amine analogues.

Accordingly to these results, the deprotection of benzaldehyde derivatives can be done by any nitroaniline analogues as long as solubility conditions are fixed.

TABLE 1

Purity analysis by High Performance Liquid Chromatography of 2-Methoxy-5-trifluoromethoxybenzylidene from corresponding imine

| Corresp. Imine Substrate [FROM SCHEME 2 ABOVE] | Lot # | H38680-127 Area % | Relative Retention Time 0.36 | Relative Retention Time 0.59 | Relative Retention Time 0.69 | Relative Retention Time 0.74 |
|---|---|---|---|---|---|---|
| — |  | 2.4 | — | 0.1 | 0.2 | 0.5 |
| — |  | 1.5 | — | — | — | — |
| 1 |  | 0.4 | 0.06 | — | — | 0.1 |
| 1 |  | 0.6 | — | — | 0.07 | 0.08 |
| 1 |  | — | — | — | — | 0.3 |
| 1* |  | — | — | — | — | 0.2 |
| 2 |  | — | — | — | 0.1 | — |
| 3 |  | — | — | — | — | — |
| 4 |  | 0.5 | — | — | 0.08 | — |
| 5 |  | 0.2 | — | — | 0.08 | 0.5 |

All were made from the normal lot.

All compounds show a important decrease of impurity. Moreover, compounds (2-Methoxy-5-trifluoromethoxybenzylidene)-(3-nitrophenyl)amine and 2-Methoxy-5-trifluoromethoxybenzylidene)-(4-methyl-2-nitrophenyl)amine in which corresponding imine were made from 3-methyl-3-nitroaniline and 4-methyl-2-nitroaniline respectively and 2-Methoxy-5-trifluoromethoxybenzylidene)-(3-nitrophenyl)amine which was made from 3-nitroaniline present a complete elimination of the regio-isomer.

TABLE 2

Source of starting material

| Product | Company | Lot Number |
|---|---|---|
| 3-nitroaniline | Aldrich | 05720TG |
| 3-methyl-2-nitroaniline | Aldrich | 04406LV |
| 4-methyl-2-nitroaniline | Eastman Organic Chemistry | Not specified |
| 2-methyl-3-nitroaniline | Aldrich | 0211AJ |
| 4-methyl-3-nitroaniline | Aldrich | 080877 |

TABLE 3

Elemental Analysis

| # | IUPAC name | Mass | Theoretical Values | | | Obtained Values | | | Offset % | | |
|---|---|---|---|---|---|---|---|---|---|---|---|
|   |   |   | C | H | N | C | H | N | C | H | N |
| 1 | (2-Methoxy-5-trifluoromethoxybenzyl-idene)-(3-nitrophenyl)amine | 340 | 52.95 | 3.26 | 8.23 | 52.95 | 3.06 | 8.20 | −0.40 | −6.44 | +1.46 |
| 2 | (2-Methoxy-5-trifluoromethoxybenzyl-idene)-(4-mehtyl-2-nitrophenyl)amine | 354 | 54.24 | 3.70 | 7.91 | 54.23 | 3.34 | 8.34 | −2.27 | +15.41 | +5.44 |
| 3 | (2-Methoxy-5-trifluoromethoxybenzyl-idene)-(3-mehtyl-2-nitrophenyl)amine | 354 | 54.24 | 3.70 | 7.91 | 53.36 | 3.35 | 7.82 | −1.62 | −9.46 | −1.14 |
| 4 | (2-Methoxy-5-trifluoromethoxybenzyl-idene)-(2-methyl-3-nitrophenyl)amine | 354 | 54.24 | 3.70 | 7.91 | 53.90 | 3.39 | 7.85 | −0.65 | −7.67 | +1.58 |
| 5 | (2-Methoxy-5-trifluoromethoxybenzyl-idene)-(4-mehtyl-3-nitrophenyl)amine | 354 | 54.24 | 3.70 | 7.91 | 54.22 | 3.36 | 7.88 | −0.04 | −9.19 | −0.38 |

EXAMPLE I

Formation of (2-Methoxy-5-trifluoromethoxybenzylidene)-(3-nitrophenyl)amine:

In a flask containing 3-nitroaniline (6.27 g, 45.4 mmol) was added hexane (140 ml) and ethanol (10 ml) and stirred vigorously to make the heterogeneous solution. It was heated to 55° C. and then 2-methoxy-5-trifluoromethoxybenzaldehyde (10 g, 45.4 mmol) was added. The solution then became orange clear. It was then stirred for 15 minutes and slowly cooled down to room temperature. The solid appeared at 31° C. The solid was filtered and washed with cold hexane to give a yellow powder (13.63 g, 88.2%).

The solid (3 g) was recrystallized in hexane (120 ml) and EtOH (2 ml). At 55° C. the solution went clear and was cooled down to 32° C. at which time big particles appeared. The temperature was maintained at 32–37° C. for 1 hour at which a wadding like solid appeared and replaced the big particles. The solution was cooled down to 0° C. The solid was filtered and washed with cold hexane to a white solid (2.66 g, 88.6%) named above.

EXAMPLE II

Formation of 2-methoxy-5-trifluoromethoxybenzaldehyde:

In a flask containing 2-Methoxy-5-trifluoromethoxybenzylidene)-(3-nitrophenyl)amine (0.4 g, 1.18 mmol), added hexane (20 ml) and HCl (20 ml). It was stirred vigorously for less than 2 hours. The layers were separated and the organic one was washed with HCl 5 M. 2-Methoxy-5-trifluoromethoxybenzylidene gave a really light yellow oil (0.210 g, 81%). Overall yield: 63.3%.

TABLE 3

Modification of the general procedure according to each substrate

| Substrate | Protection conditions | Recrystallization | Deprotection conditions |
|---|---|---|---|
| 2 | Solvent: EtOH (5 vol)<br>Reaction temp: RT to 0° C.<br>33.5% | None | Overnight stirring<br>(increase HCl conc.?)<br>75.3% |
| 3 | Solvent: EtOH (1 vol)<br>Hexane (10 vol)<br>Reaction temp: 60° C.<br>26.9% | None | Overnight stirring<br>(increase HCl conc.?)<br>— |
| 4 | Solvent: EtOH (5 vol)<br>Hexane (10 vol)<br>Reaction temp: 60° C.<br>66.2% | None | 1 hour stirring<br>86.0% |
| 5 | Solvent: EtOH (2.5 vol)<br>Hexane (10 vol)<br>Reaction temp: 60° C.<br>74.3% | None | ~3 hours stirring<br>64.5% |

TABLE 4

All reaction conditions tried and corresponding yield.

| Substrate | Condition (for 1 g of CP-130,209) | Result |
|---|---|---|
| 1 | Solvent: MeOH (10 vol)<br>Room temperature | 67%<br>Yellow solid |
| | Solvent: EtOH (10 vol)<br>Room temperature | 50.8%<br>Light yellow solid |
| | Solvent: MeOH (10 vol)<br>Temperature : 55° C. | 9.22%<br>Light yellow solid |
| | Solvent: 25% EtOH/Hexane (15 vol)<br>Temperature: 60°C. | 81%<br>Light yellow solid<br>88.2% |
| | Solvent: 6.6% EtOH/Hexane (15 vol)<br>Temperature: 55°C. | Light Yellow solid |
| 2 | Solvent: MeOH (10 vol)<br>Temperature: 60° C. | 53 mg. Seemed to be the good product. |
| | Solvent: EtOH (5 vol)<br>Temperature: 60° C. | 33.5%<br>Fluffy yellow solid |
| | Solvent: 60% EtOH/hexane (5 vol)<br>Temperature: 55° C. | Stayed soluble |
| 3 | Solvent: MeOH (8 vol)<br>Room temperature | Stayed soluble |
| | Solvent: MeOH (3 vol)<br>Room temperature | 0.256 g<br>yellow solid |
| | Solvent: EtOH (1 vol)<br>Room temperature | 75.7%<br>yellow, impure |
| | Solvent: EtOH (3 vol)<br>Room temperature | 51.7%<br>yellow impure |
| | Solvent: 10% EtOH/hexane (5 vol)<br>Temperature: 60° C. | No reaction |
| 4 | Solvent: 40% EtOH/Hexane (10 vol)<br>Temperature: 56° C. | Stayed soluble |
| | Solvent: EtOH (2 vol)<br>Room temperature | Stayed soluble |
| | Solvent: EtOH (2 vol)<br>Temperature: 0° C. | 78.8%<br>Light yellow solid |
| | Solvent: 10% EtOH/hexane (10 vol)<br>Temperature: 60° C. | 74.3%<br>Very light yellow |
| 5 | Solvent: 40% EtOH/hexane (10 vol)<br>Temperature: 60° C. | Stayed clear |
| | Solvent: EtOH (3 vol)<br>Room temperature | 63.2%<br>Beige powder |
| | Solvent: EtOH (4 vol)<br>Room temperature | 66.2%<br>White-beige powder |
| 6 | Solvent: 6.6% EtOH/Hexane (15 vol)<br>Temperature: 60° C. | Insoluble |
| | Solvent: MeOH (10 vol)<br>Room temperature | Stayed soluble |
| | Solvent: 20% EtOH/Hexane (15 vol)<br>Temperature: 58° C. | Insoluble |
| | Solvent: 33% EtOH/Hexane (15 vol)<br>Temperature: 60° C. | Stayed soluble |
| | Solvent: MeOH (2 vol)<br>Temperature: 60° C. | Stayed soluble |
| | Solvent: EtOH (3 vol)<br>Temperature: 60° C. | No reaction |
| 7 | Solvent: 6.6% EtOH/Hexane (15 vol)<br>Temperature: 57° C. | Insoluble |
| | Solvent: EtOH (15 vol)<br>Temperature: 50° C. | Stayed soluble |
| | Solvent: MeOH (5 vol)<br>Temperature: 50° C. | Stayed soluble |
| | Solvent: MeOH (2 vol)<br>Temperature: 60° C. | Stayed soluble |
| 8 | Solvent: 6.6% EtOH/hexane (15 vol)<br>Temperature: 54° C. | Insoluble |
| 9 | Solvent: 6.6% EtOH/hexane (15 vol)<br>Temperature: 58° C. | Insoluble |
| | Solvent: 20% EtOH/EtOAc (10 vol)<br>Temperature: 58° C. | Insoluble |
| | Solvent: MeOH (10 vol)<br>Temperature: 60° C. | Insoluble |
| | Solvent: EtOH (3 vol)<br>Temperature: 60° C. | Insoluble |
| 10 | Solvent: MeOH (10 vol)<br>Temperature: 60° C. | Stayed soluble |
| | Solvent: MeOH (4 vol)<br>Room temperature | 0.83 g.<br>Orange yellow solid. |
| | Solvent: 40% EtOH/hexane (10 vol)<br>Temperature: 62° C. | Stayed soluble |
| 11 | Solvent: MeOH (10 vol)<br>Temperature: 60° C. | Stayed soluble |
| | Solvent: MeOH (3 vol)<br>Temperature: 60° C. | Stayed soluble |

What is claimed is:

1. A process for the purification of 2-methoxy-5-trifluoromethoxy benzaldehyde comprising
   (a) converting said oil to an imine by reaction of a nitroaniline with said oil,
   (b) isolating said imine as a solid and;
   (c) converting back said solid imine is to said 2-methoxy-5-trifluoro-methoxy benzaldehyde oil.

2. The process according to claim 1 wherein the nitroaniline is selected from the group consisting of 3 nitroaniline, 3-methyl-2-nitroaniline, 4-methyl-2-nitroaniline, 2 methyl-3-nitroaniline and 4-methyl-3-nitroaniline.

3. The process according to claim 1 wherein the imines are selected from the group consisting of
   (2-Methoxy-5-trifluoromethoxybenzylidene)-(3-nitrophenyl)amine;
   (2-Methoxy-5-trifluoromethoxybenzylidene)-(4-mehtyl-2-nitrophenyl)amine;
   (2-Methoxy-5-trifluoromethoxybenzylidene)-(3-mehtyl-2-nitrophenyl)amine;
   (2-Methoxy-5-trifluoromethoxybenzylidene)-(2-methyl-3-nitrophenyl)amine;
   (2-Methoxy-5-trifluoromethoxybenzylidene)-(4-mehtyl-3-nitrophenyl)amine;
   (2-Methoxy-5-trifluoromethoxybenzylidene)-(4-nitrophenyl)amine;
   (2-Methoxy-5-trifluoromethoxybenzylidene)-(3,5-dinitrophenyl)amine;
   (2-Methoxy-5-trifluoromethoxybenzylidene)-(1,6-dinitrophenyl)amine;
   (2-Methoxy-5-trifluoromethoxybenzylidene)-(2,4-dinitrophenyl)amine;
   (2-Methoxy-5-trifluoromethoxybenzylidene)-(5-methyl-2-nitrophenyl)amine; and
   (2-Methoxy-5-trifluoromethoxybenzylidene)-(6-methyl-2-nitrophenyl)amine.

4. The process according to claim 1 wherein the temperature range to precipitate the imine is about 30 to about 40° C.

5. The process according to claim 1 wherein the solvent used to recrystallize the imine is selected from the group consisting of ethanol, methanol and ethanol/hexane.

6. The process according to claim 1 wherein the solvent used to recrystallize the 2-methoxy-5-trifluoromethoxy benzaldehyde is a mixture of hexane and hydrochloric acid.

* * * * *